United States Patent [19]

Fathman

[11] Patent Number: 4,681,760
[45] Date of Patent: Jul. 21, 1987

[54] METHOD OF CONFERRING IMMUNOTOLERANCE TO A SPECIFIC ANTIGEN

[75] Inventor: C. Garrison Fathman, Menlo Park, Calif.

[73] Assignee: The Board of Trustees of the Leland Stanford Junior University, Stanford, Calif.

[21] Appl. No.: 724,063

[22] Filed: Apr. 17, 1985

[51] Int. Cl.⁴ .................... A61K 39/00; A61K 39/35; A61K 39/395
[52] U.S. Cl. ....................................... 424/85; 424/86; 424/87; 424/88; 424/89; 424/90; 424/91; 424/92; 514/885; 435/810; 436/548; 436/512; 436/506; 436/811; 436/547
[58] Field of Search .................................. 424/85–92; 435/7, 810; 436/548, 512, 506, 811, 547

[56] References Cited

U.S. PATENT DOCUMENTS

| | | | |
|---|---|---|---|
| 4,366,246 | 12/1982 | Riggs | 536/27 |
| 4,478,823 | 10/1984 | Sanderson | 260/112 B |
| 4,489,710 | 12/1984 | Spitler | 424/85 |
| 4,511,502 | 4/1985 | Guilder et al. | 435/60 |
| 4,511,503 | 4/1985 | Olson et al. | 435/60 |
| 4,520,226 | 5/1985 | Neville et al. | 436/548 |
| 4,550,086 | 10/1985 | Reinherz et al. | 424/85 |

FOREIGN PATENT DOCUMENTS 0097518  1/1984  European Pat. Off. ............ 436/548

OTHER PUBLICATIONS

Dialynas et al, "Characterization of the Murine T Cell Surface Molecule ... Leu 3/T4 Molecule", *J. of Immunology*, vol. 131(5) 1983, p. 2445.
Cobbold et al, "Therapy with Monoclonal Antibodies by Elimination of T-Cell Subsets in vivo", *Nature* 312, 1984, pp. 548–551.
Kan et al, "Noncovalently Bonded Subunits of 22 and 28 KI . . . Antibody", *J. of Immunology*, vol. 131(2) 1983, pp. 536–539.
Jonker et al, "Effects of in vivo Administration of Monoclonal Antibodies ... Model", C.A. vol. 99, 1983, #120478c.
Marrack et al, "The Major Histocompatibility Complex-Restricted . . . T Cells", CA vol. 99, 1983, #210897t.
Miller et al, "In vivo Effects of GK1.5 (Anti-L3T4a) Monoclonal Antibody ... Hypersensitivity", C.A. vol. 102, 1985, #219387g.
Wofsy, D., et al, abstract submitted to WSCI, Feb. 4–6, 1985.
Woodcock, J., et al, abstract submitted to Western AFCR, Feb. 4–6, 1985.
Wofsy, D., et al, abstract submitted to Western AFCR, Feb. 4–6, 1985.

*Primary Examiner*—John Kight
*Assistant Examiner*—Garnette D. Draper
*Attorney, Agent, or Firm*—Ciotti & Murashige

[57] ABSTRACT

A method of selectively suppressing the immune system and conferring immunotolerance against a specific antigen by interferring with the L3T4 differentiation antigens on helper T cells is described. Simultaneous administration of a binding moiety specific for the L3T4-equivalent in the subject species and a specific antigen results in a diminished ability of the subject to respond immunologically to the antigen, whether or not the subject has been exposed previously to the antigen.

20 Claims, 2 Drawing Figures

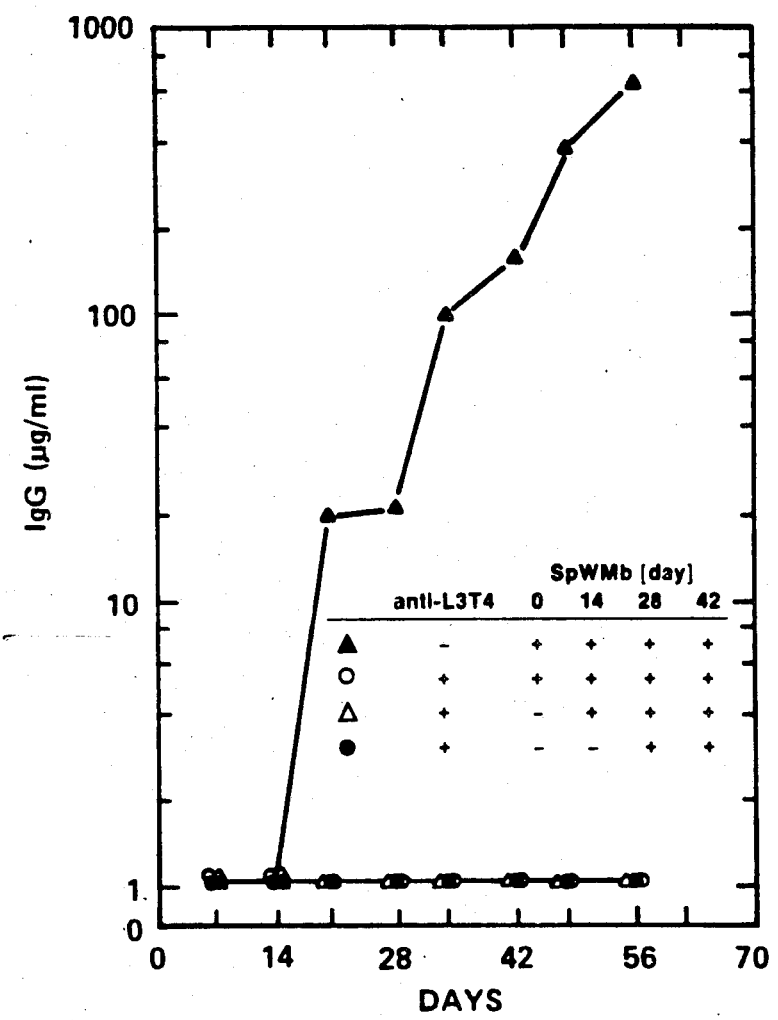

METHOD OF CONFERRING IMMUNOTOLERANCE TO A SPECIFIC ANTIGEN

REFERENCE TO A GOVERNMENT GRANT

The Government has rights in this invention pursuant to NIH Grant No. A1-18716 awarded by the Department of Health and Human Services.

TECHNICAL FIELD

The invention relates to methods of modulating a specific immune response, including control of unwanted immune reactions to pharmaceuticals, allergic reactions, and organ allograft tolerance inductions. In particular, binding moieties against the T cell differentiation antigen of the subject species which corresponds to the murine differentiation antigen L3T4 are useful in preventing both primary and secondary immune responses to a simultaneously administered immunogen.

BACKGROUND ART

The efficient functioning of the immune system is a double-edged sword. Its ability to provide a defense against invasion by hostile foreign organisms such as infectious bacteria, viruses, or even malignant cells is relied upon by vertebrate organisms for their health; indeed, their viability depends upon the success of this protection. On the other hand, there are some undesirable side effects to this efficiency, even as it relates to foreign substances encountered by the host. Not all intrusions of foreign tissue are necessarily hostile. Problems encountered in rejections of skin grafts for burn victims has a long history; the more recent proliferation of procedures which involve organ transplants has brought the problem of foreign tissue rejection to the attention of the general public.

Furthermore, it has come to be understood that allergic responses result from operation of the immune system. Allergens apparently trigger responses which culminate in formation of antibodies some, (IgE), capable of binding to mast cells, to elicit the unpleasant symptomology associated with allergies. These sysmptoms may be merely unpleasant, or may be severe, as are those encountered in patients allergic to certain medications, such as penicillin. The advent of pharmaceutical compositions containing peptide molecules large enough to be immunogenic has magnified the importance of this problem. Peptide pharmaceuticals useful in a variety of treatments such as antiviral and anticancer therapies have recently been made much more readily available through recombinant techniques.

It is common knowledge that attempts to prevent unwanted immune responses have not been particularly successful. For example, efforts are made to match transplant recipients with donors so as to minimize the amount of immunogenic response to foreign materials. Only in the case of identical twins can reasonable success be certain. The limitations of such an approach are so apparent as to warrant no further comment. Alternatively, brute force efforts to suppress the immune system in general, such as administration of anti-mitotic agents may prevent rejection at the expense of the recipient's life due to the resulting susceptibility to infection.

An alternate approach applicable only to preventing tissue rejection is passive immunization of recipients with antibodies directed against the histocompatibility antigens (Davies, D. A. L., et al, *Transplant Reviews* (1979) 30:18–39). Other approaches also applicable only to the transplant rejection problem have employed treatment of the donor tissue. These are based on the assumption that the rejection response is caused by the histocompatibility antigens on the surface of passenger leukocytes carried on the transplant which leukocytes are not an essential part of the desired tissue per se. In vivo culture of the donor transplant tissue has been used to eliminate passenger leukocytes (*Surgery* (1977) 81:74–79; *Science* (1980) 209:283–285; *Trans Proc* (1982) 8:1094–1098). The donor tissue has also been treated directly with suitable antibodies (Faustman, D., et al, *Transplantation* (1982) 34:302–305). Copending U.S. application Ser. No. 532,609, filed Sept. 15, 1983, assigned to the same assignee, and incorporated herein by reference, discloses the use of immunotoxins formed by conjugating antibodies with a cytotoxic moiety for pretreatment of donor tissue.

Methods to prevent immune responses to soluble antigens have been largely confined to avoidance of exposure. Patients allergic to certain drugs are treated with alternative formulations when available; hay fever sufferers attempt to stay away from the immunogenic pollen. If avoidance is impossible, one must resort to treating the symptoms.

What is desired is a specific immuntolerance with respect to a particular antigen, leaving the general competence of the immune system intact. None of the foregoing approaches achieve such a selective immunosuppression of the subject. Treatments employed to prevent transplant rejection which are directed toward the host per se generally depress the entire system; treatments of the donor tissue alter the nature of the foreign material introduced. In the case of allergic responses to drugs or to environmental antigens, alteration of the foreign material is either undesirable or impractical. In the present invention, the immune system of the host is selectively and specifically suppressed with respect to a particular immunogen without impairing general immunocompetence. The invention achieves this result by virtue of its specificity for a differentiation antigen on the surface of helper T cells, thus preventing those cells from participating in mounting an immune response against a specified, simultaneously introduced, antigen.

DISCLOSURE OF THE INVENTION

The present invention provides a method for suppressing undesired immune responses, such as allergic reactions, to antigens whose administration to the subject is either desired or inevitable but otherwise harmless. It also provides a method for inducing tolerance to tissue transplants.

In one important application, the advent of recombinant technology has made available a substantial number of potentially powerful therapeutic polypeptides such as, for example, the interferons or interleukins, which often elicit an unwanted immune response. Of course, allergic reactions to more commonly used drugs are not unknown, but the new polypeptide pharmaceuticals, presumably because of their size, are more troublesome in this regard. The invention permits the subject to experience the desirable therapeutic effects of a desired drug without the immunologic reaction.

Another application is to the problem of allergies to foods or materials in the surroundings. Millions of individuals are subjected to severe symptomology in response to otherwise perfectly harmless components of the environment, for example, ragweed or other pollens. The method of the invention can prevent or diminish this immune response which results in widespread discomfort.

A third application, to reduce the incidence of tissue rejection in transplant procedures, is significant in making these often life saving procedures safe and practical. These procedures could, in this era, otherwise be straightforward absent the problems of incompatability.

A fourth application is to allow the use of foreign proteins such as xenogeneic monoclonal antibodies for therapy of certain diseases such as cancer.

The method of the invention resides in the co-administration of the antigen for which immunotolerance is sought and an antibody which is specific for the "L3T4-equivalent" differentiation antigen on T cells, thus preventing these helper T cells from participating in the immune response otherwise concurrently mounted against the particular co-injected or co-administered antigen. The protective antibodies may be administered directly, or these antibodies or L3T4-equivalent binding portions thereof may be conjugated with cytotoxic moieties to obtain immunotoxic conjugates. The cytotoxic moieties may aid in the destruction of the helper T cell function which is also prevented by reaction with the antibodies alone. The essential component of the protective composition is the L3T4-equivalent specific binding moiety.

Two general situations are of interest. One relates to a naive subject, previously unexposed to the antigen of concern. This is commonly the case with respect to transplant hosts or patients who are to be treated with new or infrequently administered drugs. The other relates to individuals previously exposed to the same antigen. This is most often the case for allergic responses to components of the environment.

With respect to defensive immunosuppression against a previously unencountered agent, such as a new pharmaceutical or transplant, it is sufficient to suppress the primary immune response to introduction of the foreign substance. In the method of the invention, this primary response is suppressed by administration of the binding moiety, e.g., antibody or immunotoxin specifically immunoreactive with the differentiation antigen corresponding to the murine L3T4 surface glycoprotein in the subject species (i.e., an "L3T4-equivalent") simultaneously with the administration of the foreign substance. Accordingly, the invention in one aspect relates to a method of preventing or ameliorating the immune response to an immunogen by simultaneous administration of the anti-L3T4-equivalent moiety along with the immunogenic substance.

With respect to alleviation of responses to previously experienced immunogens, the technique is the same although the history of the subject, and therefore the subject itself, is different. The nature of the response is also different. While the most frequent instance of such prior exposure is in the case of environmental allergens, this aspect of the invention is not limited to such allergens per se. Previous exposure to the same allergen is the norm, and the invention is particularly useful in this application. Even this response to a secondary challenge with the immunogen can be mitigated by simultaneous administration of the immunogen along with L3T4-equivalent binding moiety before the "booster" exposure. Alternatively, the binding moiety can be administered contemporaneously with the booster exposure, this exposure itself serving as the simultaneously administered antigen. Accordingly, the invention in another aspect relates to amelioration of a secondary immune response, most commonly, an allergic response, by administering to a subject, previously exposed to an immunogen, a simultaneous dose of immunogen and the suitable L3T4-equivalent specific moiety.

In another aspect, the invention contemplates kits containing compositions suitable for effecting the method of the invention.

MODES OF CARRYING OUT THE INVENTION

Introduction

Figure 1:
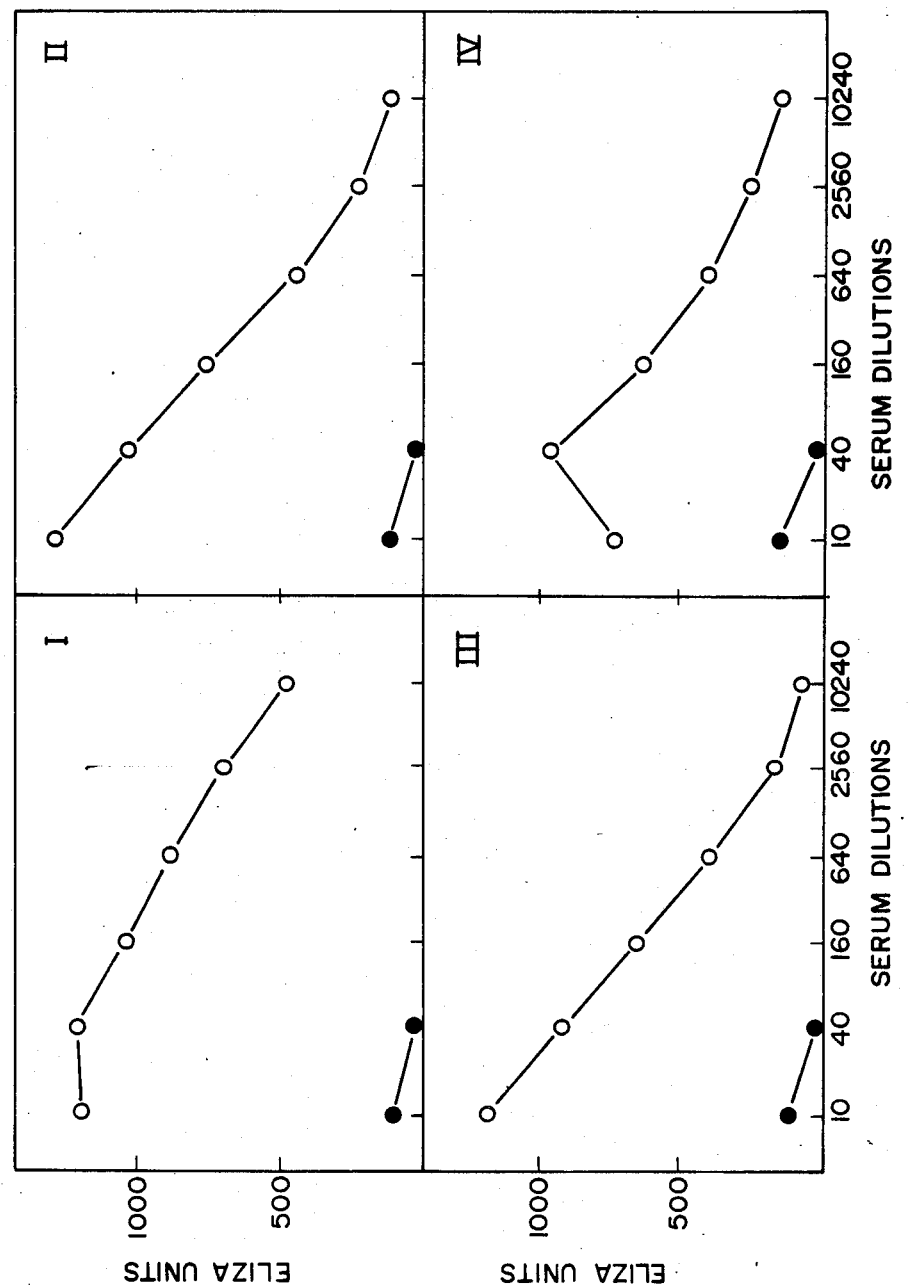
FIG. 1 shows the total specific anti-myoglobin immunoglobulin levels obtained in mice with and without simultaneous injection with GK1.5 monoclonal antibody (Mab).

The method of the invention depends on the interruption of a specific immune response by crippling the participation of a subclass of T lymphocytes, the helper cells. These cells are recognized by a surface-borne glycoprotein differentiation antigen, designated L3T4 in the murine system.

Briefly, it has long been established that two major types of lymphocytes participate in the immune response--T cells, which differentiate to various effector functions, and B cells, which differentiate so as to secrete specific antibodies to the antigen. In a very general way, the primary function of the B lymphocyte differentiated cells (plasma cells) is to secrete antibody; the differentiated T cells provide effector functions such as those of the killer cells, helper cells, and suppressor cells. T cells, in addition to antigen-specific recognition sites, contain differentiation antigens characteristic of their particular subtype. Accordingly, the method of the invention influences the course of the immune response by blocking the characteristic differentiation antigen of the helper T cell subtype, thus inhibiting the effector function of the helper T cells.

The helper cells apparently interact with B cells to "help" effect B cell differentiation and proliferation; in addition, they "help" in the differentiation of T cells into their effector roles, e.g., as killer cells. A majority of these helper T lymphocytes (HTLs) contain a surface differentiation antigen designated in the murine system as L3T4. This differentiation antigen is a glycoprotein of apparent molecular weight 52,000 (Dialynas, D. P., et al, J Immunol (1983) 131:2445-2451) and is apparently analogous to the Leu3 or T4 differentiation antigen on human helper T cells. Monoclonal antibodies (Mabs) specific to the L3T4 differentiation antigen have been prepared (Dialynas, D. P., et al, (supra)). A hybridoma secreting such monoclonal antibodies, designated GK1.5, was obtained from a fusion of a mouse nonsecretor myeloma SP2/O with spleen cells from a rat that had been injected with a cloned T cell line. The Mabs secreted are rat IgG2b antibodies specific against L3T4.

Others have investigated the effect of the injection of GK1.5 Mabs on the immune response. Wofsy, D., et al, in a paper presented to WSCI, Feb. 4–6, 1985, reported that weekly injections of anti-L3T4 antibody into a strain of mice prone to develop autoimmune disease decreased the circulating levels of L3T4-positive cells by 90%–95% and suppressed the development of autoimmunity. They further observed that the mice developed little or no antibody to the rat IgG. Woodcock, J., et al, in an abstract submitted to Western AFCR February 4–6, 1985 disclosed that intravenous injection into mice of the GK1.5-derived IgG2b monoclonal antibody 3 days before a xenogeneic skin graft delayed the time of rejection. The injected mice showed a reduction of L3T4-positive cells even after 28 days. Additional administrations of the monoclonal antibody enhanced the reduction of circulating L3T4-positive cells. The results are consistent with those of Cobbold, S. P., et al, *Nature* (1984) 312:548–551, which show that IgG2b antibodies are successful in eliminating T cell subsets bearing this marker in vivo.

Wofsy, D., et al, in an abstract submitted to the Western AFCR, Feb. 4–6, 1985, report the effect of GK1.5-secreted Mab injection on the immune response to a soluble antigen. Mice injected with bovine serum albumin (BSA) normally produced anti-BSA IgM immediately followed by a rapid increase in the level of anti-BSA IgG antibodies. The IgG response could be prevented by a single injection of the GK1.5-secreted Mabs within 48 hours of immunization, but suppression of IgG function did not occur if injection was made more than 48 hours after the administration of BSA. Wofsy also observed that injections of GK1.5 Mabs into mice did not elicit an immune response, whereas treatment with other rat IgG2b Mabs did stimulate high titers of anti-rat antibody.

A. DEFINITIONS

As used herein "simultaneously" when referenced to injection of antigen and L3T4-equivalent binding moiety refers to injection or administration of one within approximately 48 hours of the other. Either may be administered first. It is preferable, however, that the administration of the binding moiety be carried out substantially contemporaneously with or within 48 hours prior to injection or other administration of the antigen.

"L3T4-equivalent binding moiety" refers to a substance which is specific to the differentiation antigen corresponding in the subject species to the L3T4 surface differentiation antigen of murine HTL cells. Some moieties may be immunoreactive against a determinant on these differentiation antigens which makes them cross-reactive with the correspondant differentiation antigens on HTL cells in several species. In general, because of the powerful immunosuppressant activity of the antibodies useful in this invention, it is not necessary that they be derived from the subject species. For example, the rat IgG2b monoclonal antibody GK1.5 is reactive against murine L3T4 and these Mabs are convenient for use in murine test systems since they do not raise antibodies to rat Ig in mice. Other commercially available monoclonal antibodies, such as Leu3 (Becton Dickinson) or T4 (Ortho) are reactive against human Leu3 or T4 differentiation antigen. Various alterantive hybridoma lines producing monoclonal antibodies which specifically react with the corresponding differentiation antigens in T cells of the subject are suitable in the method of the invention.

It is not, of course, necessary that monoclonal antibodies be used as the L3T4-equivalent binding moiety. Monoclonal antibody preparations have the advantage of higher affinities and homogeneity, but polyclonal preparations may be used. Also, fragments of immunoglobulins which retain target specificity, for example, F(ab)$_2$ fragments are useable as well. In addition, antibodies specific against L3T4-equivalents or fragments thereof may be conjugated with cytotoxins. The construction of immunotoxins using various cytotoxic moieties, such as whole ricin, ricin A, diphtheria toxin, pokeweed antiviral protein (PAP) or other naturally occurrring or artificial toxins are by now well understood in the art. For reviews, see Thorpe, P. E., et al, *Immunol Revs* (1982) 62:119–158; Jantzen, et al. (ibid) pp 185–216; Olsnes, S., et al, *Pharm Ther* (1982) 15:335–381.

Thus, in summary, the term L3T4-equivalent binding moiety refers to monoclonal or polyclonal antibodies or fragments thereof or any of these bound to cytotoxins, so long as the specific ability to bind the L3T4-equivalent in the species of interest is retained.

"Specific antigen" refers to the immunogenic substance of interest. Thus, specific antigens include globular proteins, glycoproteins such as immunoglobulins, materials carried on particles such as pollen proteins, polypeptides intended for therapeutic use such as interferon, interleukin-2, or tumor necrosis factor, hormone replacements, such as leutinizing hormone or its analogs or antagonists, and the like. Synthetic peptide analogs of protein therapeutic agents which are used for receptor blockade are another important class of soluble antigen. Still another important subclass is that of alloantigens, i.e., those which are products of the major histocompatibility complex. It is these allo-antigens which are presumably responsible for rejection of foreign tissue in tissue transplants or skin grafts.

A significant aspect of the invention is that it is efficacious regardless of whether or not the subject has been previously exposed to the antigenic substance because it provides immunotolerance to a specific antigen upon secondary as well as primary exposure. Primary responses to antigens generally involve formation of quantities of IgM antibodies specific to the antigen. "Booster" exposures to the antigen (or, indeed, the delayed response to the initial administration) result in a secondary response-comparatively dramatic increases in the Igg, IgA, and IgE population specific to the antigen. In other words, the secondary response is characterized by an increase in specific IgG, IgA, and IgE levels. The IgM population fairly quickly diminishes and is again supplemented only when an additional administration of the antigen is made; IgG, IgA, and IgE levels are maintained for longer periods. Previous exposures to the same antigen result in an enhanced secondary response upon subsequent exposure.

B. GENERAL METHOD

The essential feature of the invention is administration of the binding moiety of correct specificity to block the subject's "L3T4" differentiation antigen or, more precisely, the subject species' correspondant surface glycoprotein simultaneously with administration of the specific antigen. The actual effect of the binding moiety may be to kill the L3T4-equivalent-bearing cells or to block the effector function of these cells in some noncytotoxic event. Accordingly, it may enhance the effectiveness of the L3T4-equivalent binding moiety to prepare it as an immunoconjugate with a cytotoxic material. The cytotoxin will thus be directed specifically to the target T helper cells.

THE L3T4-EQUIVALENT BINDING MOIETY

The dosage of the L3T4-equivalent binding moiety which is administered will depend on its form, on whether or not it is converted to an immunotoxin, on its mode of administration, and on the condition of the subject. Clearly the most preferred mode of administration is by injection, preferably intravenous injection. Typically, the subject to be thus specifically immunosuppressed is injected with about 200 mg–5 g, preferably about 1–2 g of L3T4-equivalent binding moiety in a suitable excipient, such as physiological saline, in a single injection intravenously or intraperitoneally.

The antibody portion of the desired binding moiety is obtained by conventional procedures. L3T4-equivalent sera may be obtained from immunized subjects. For the Leu3 or T4-equivalent human differentiation antigen, antisera may be prepared from subject mammals such as mice, horse, goat, rabbit, sheep, or rats by injecting with human helper T cells and collecting the sera from the immunized host. Since the L3T4-equivalent binding moiety confers selective specific immunosuppression, the use of non-human antisera is permissible. Antibodies desired for other mammalian subjects may be similarly derived using injections of helper T cell subpopulations from these mammals.

Monoclonal anti-L3T4-equivalent antibodies may also be made by the somatic cell hybridization procedure first described by Kohler, G., et al, *Nature* (1985) 256:495–497. The immortalizing cell lines, reagents, and conditions used in this procedure are well known. Briefly, the procedure involves immunizing the host as above, collecting antibody-producing cells and fusing these cells with an appropriate immortalizing cell line using a fusogen such as polyethyleneglycol, growing the cells in selective medium to eliminate unhybridized partners, identifying hybridomas that produce antibodies against the immunogen, culturing these hybridomas and collecting the Mabs from the resulting culture fluid. The immortalizing partner used for the fusion also need not confer characteristics on the Mab which are compatible with the subject, because of the specific immunosuppression conferred. As stated above, anti-L3T4-equivalent monoclonal antibodies are available commercially for humans and for a number of other species.

Antigen binding fragments (F(ab), F(ab'), $F(ab')_2$, F(v)) of polyclonal or monoclonal antibodies are made by digesting the whole immunoglobulin with an appropriate protease, for example, papain in the case of F(ab) and pepsin in the case of $F(ab')_2$. The class (and subclass) of the antibody used is not critical. Polyclonal antisera presumably are mixtures of Ig classes; Mabs produced are of a single subclass.

If the L3T4-equivalent binding moiety is administered as an immunotoxin, the antibody portion is conjugated using standard conjugation techniques to a cytotoxin. Thorpe, P. E., et al (supra); Olsnes, S., et al (supra). Typical coupling agents include, for example, 3, 3'-dimethyl-dithio(bis)propionate, and N-succinnimidyl-3-(2-pyridyl-dithio)propionate (SPDP) which yield a reducible disulfide bond; and, for example, the N-hydroxysuccinnimdyl esters of, for example, 6-maleimidylcaproic acid which yield thioethers. Other coupling agents, such as glutaraldehyde or carbodiimides yield alternate chemistries.

The cytotoxin moiety may, for example, be a bacterial or plant toxin, or a portion thereof that includes its enzymatically active fragment or a similarly active protein. Examples of such toxins are diphtheria toxin, *Pseudomonas* exotoxin, ricin, abrin, momordin, gelonin, and the like. The toxins and proteins may be extracted from bacteria or plants or may be synthesized using known peptide synthesis techniques (if relatively short) or by recombinant techniques if the gene sequences are available.

THE SPECIFIC ANTIGEN

The amount and nature of the material used for simultaneous injection to confer the desired specific immunosuppression depends on the type of antigen.

For allergens, whether environmental or deliberately administered soluble antigens, such as drugs, the antigenic component may be conveniently administered intravenously in suitable excipients in amounts of 10 μg–1 mg. Alternatively, for environmental allergens, exposure may mimic "natural" exposure and employ aerosols or oral compositions and quantities approximating the estimated degree of exposure are appropriate. For example, one might use a "field of flowers" approach in protecting a subject against an immune response to a naturally occurring pollen. That is, at the beginning of the acacia blooming season, for example, the subject is placed in proximity to the offending blooms while simultaneously being administered protective binding moieties. Gradations between these natural exposures and the highly artificial method of isolating the specific allergen and co-injection with the L3T4-equivalent binding moiety may also be used. The nature of this administration and the formulation of appropriate pharmaceutical compositions is well known to those in the art.

If the allergen is a therapeutic agent, amounts of antigen approximating those intended to be administered and a similar route of administration may be used. In general, this protection affords a simpler problem as generally speaking the antigen is already available in a suitably formulated pharmaceutical composition and the levels of exposure expected and expected routes of administration are already known.

For suppression of rejection in the case of transplanted tissue, specifically, with respect to allografts, a variety of modes of administration are feasible. Allografts are multiplicities of cells or associated cells that define a tissue or organ from an individual of the same species as that of the intended recipient, but which derive from an individual genetically dissimilar from the recipient. These cell multiplicities themselves, include vascularized organs such as heart, kidney, liver, lungs, etc. Additionally endocrine glands (pituitary, thyroid, adrenal, parathyroid, and pancreas) or skin grafts may not contain the major histocompatibility antigens which are responsible for triggering the rejection of the transplant. These antigens are carried by passenger cells such as leukocytes which are included in the transplanted cells as impurities.

Two general approaches may be used: the transplant materials can themselves be used as a source of antigen, or the particular histocompatibility antigens may be obtained separately and administered alone or as cells bearing the histocompatibility antigens of the transplant donor, i.e., peripheral blood lymphocytes. A major antigen responsible for tissue rejection carried on such passenger leukocytes is the murine Ia-equivalent antigen which in humans is designated HLA-DR (MHC class II antigens). Human HLA-DR antigens have been subclassified and if the donor has been typed, suitable antigen, e.g., peripheral blood lymphocytes, associated with the donor tissue is conveniently obtainable and injected prior to transplant along with the L3T4-equivalent binding moiety. The perhaps more crude, but effective, manner of administration is simultaneous injection of the L3T4-equivalent binding moiety along with the transplant itself or a pre-transplant simultaneous injection of a portion of the tissue suitably finely divided and formulated along with the protecting binding moiety.

FORMULATION

As seen from the previous paragraphs, each specific antigen offers alternative routes for administration appropriate to its nature. All offer the possibility of obtaining purified antigen and utilizing intravenous administration. In certain instances, it is also possible to inject a composition containing a mixture of the specific antigen along with the binding moiety in a suitable pharmaceutical composition.

In summary, for antigens in general, while intravenous administration is most convenient, other forms of administration are useful as well. Other routes of parenteral administration include subcutaneous, intraperitoneal, or intramuscular injection. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of nontoxic auxiliary substances such as wetting or emulsifying agents, pH buffering agents and the like. For substances intended to stimulate the immune system, such as the specific antigen administered in the method of the invention, an adjuvant, such as complete Freund's adjuvant is generally used.

An additional approach for parenteral administration employs the implantation of a slow-release or sustained-release system, such that a constant level of dosage is maintained.

Systemic administration may be effected via suppository. For such formulations, traditional binders and carriers include, e.g., polyalkalene glycols or triglycerides. Such suppositories may be formed from mixtures containing L3T4-equivalent binding moiety or antigen in the range of 0.5%–10%; preferably 1%–2%.

For aerosol administration, the antigen is preferably supplied in finely divided form along with a surfactant and a propellant. Typical percentages of active ingredients are 0.01% to 20% by weight, preferably 0.4% to 1.0%. Surfactants must, of course, be nontoxic, and preferably soluble in the propellant. Representative of such agents are the esters or partial esters of fatty acids, such as caproic or octanoic acids, polyols such as mannitol or sorbitol, or their anhydrides or esters and their polyoxyethylene and polyoxypropylene derivatives. Preferred surface-active agents include the oleates of sorbitan, e.g., those sold under the trademarks "Arlacel C", "Span 80", and "Span 85". The surfactant may constitute 0.1%–20% by weight of the composition, preferably 0.25%–5%. The balance of the composition is ordinarily propellant; for example the lower alkanes, such as butane and propane; and preferably fluorinated or fluorochlorinated alkanes, such as are sold under the trademark "Freon". In producing the aerosol, a container equipped with a suitable valve is filled with the appropriate propellant, containing the finely divided active ingredient and surfactant. The ingredients are thus maintained at an elevated pressure until released by action of the valve.

Solid compositions of antigen or L3T4-equivalent binding moiety may be used if administered orally or if reconstituted for administration. Conventional nontoxic solid carriers include, for example, pharmaceutical grades of mannitol, lactose, starch, or magnesium stearate. The corresponding liquid pharmaceutically administerable compositions can be prepared by dissolving, dispersing, etc, the antigen or binding moiety above and optional pharmaceutical adjuvants in a carrier as described above.

Actual methods of preparing the above dosage forms are known, or will be apparent, to those skilled in this art; for example, see *Remington's Pharmaceutical Sciences,* Mack Publishing Company, Easton, PA. 15th Edition, 1975. The composition or formulation to be administered will, in any event, contain a quantity of the binding moiety or antigen in an amount effective to obtain the desired specific immunosuppression.

KITS

It is convenient to package the specific antigen and protective L3T4-equivalent binding moiety into kits for administration of the treatment. Thus, for example, kits for the treatment of allergy would comprise containers with, preferably, unit dosage levels of allergen such as ragweed protein, milk protein, or other allergenic material in suitable excipients including most preferably adjuvant preparations such as Freund's complete adjuvant. An additional container would supply, e.g., suitable monoclonal antibodies specific for L3T4 or immunotoxins derived from them in form for administration such as a suspension in physiological saline or other pharmaceutical excipient or in solid form to be reconstituted. For certain antigen/binding moiety combinations, these components may be supplied as a mixture. Additional components of such kits might be sterile disposable syringes. All materials may be packaged in convenient containers for administration as is known in the art.

C. EXAMPLES

The following examples are meant to illustrate and are not intended to limit the invention.

EXAMPLE 1

Suppression of the Immune Response Against Myoglobin

Sperm whale myoglobin was used as a antigen in Balb/C mice, and the ability of GK1.5-secreted Mab to produce specific immunosuppression with respect to this antigen was verified using four protocols. The four protocols differed only in the timing of the injections of the antigen and protecting antibody. In each protocol, one experimental group consisting of three 6–8 week old mice, and two control groups consisting of three similar mice were used. One control group received corresponding injections of α-Thy Mab instead of GK1.5-secreted Mab at identical times and in the same amounts. The other control group received injections of corresponding volumes of buffer solution. All groups in all protocols received 100 μg myoglobin in complete Freund's adjuvant on day 0 and booster injections of 50 μg myoglobin in the adjuvant every 14 days thereafter.

Sera were collected on day 7 and day 10 after each immunization and assayed for the presence of anti-myoglobin total immunoglobulin (including both IgM and IgG) by ELISA as described in Example 3 below. The specific protocols are as follows:

Protocol 1: (Antibody and antigen were injected intraperitoneally.)
Antibody: 200 μg on days -1 and 0; 100 μg on days 1 and 2.
Antigen: 100 μg on day 0, 50 μg every 14 days thereafter.

Protocol 2: (Antibody and antigen were injected intravenously.)
Antibody: 100 μg on day 0.5, 1, 1.5, and 2. Antigen: 100 μg on day 0, 50 μg every 14 days thereafter.

Protocol 3: (Antigen and antibody were injected intravenously.)
Antibody: 100 μg on day 0, 1, and 2.
Antigen: 100 μg on days 0, 1, and 2, 50 μg every 14 days thereafter.

Protocol 4: (Antigen and antibody were injected intravenously.)
Antibody: 100 μg on day 0, 1, and 2.
Antigen: 100 μg on day 0, 1, and 2, and 50 μg every 14 days thereafter.

FIG. 1 shows the results obtained on typical bleeding for mice in each of the 4 protocols. Results are given in ELISA units (see Example 3, below) as a function of serum dilution. The data shown wre taken 9 days after six 14-day intervals post day 0 but are typical of results obtained upon earlier bleeding. The open circles show the levels of total immunoglobulin specific against myoglobin in the α-Thy injected controls. The closed circles show corresponding results for the experimental group at two serum dilutions.

All four protocols gave similar results. The controls show high levels of specific antimyoglobin immunoglobulins correlating with serum dilution. Antimyoglobin antiserum is absent from the GK1.5-secreted Mab-injected groups.

EXAMPLE 2

Suppression of Secondary Response to Myoglobin

Figure 2:
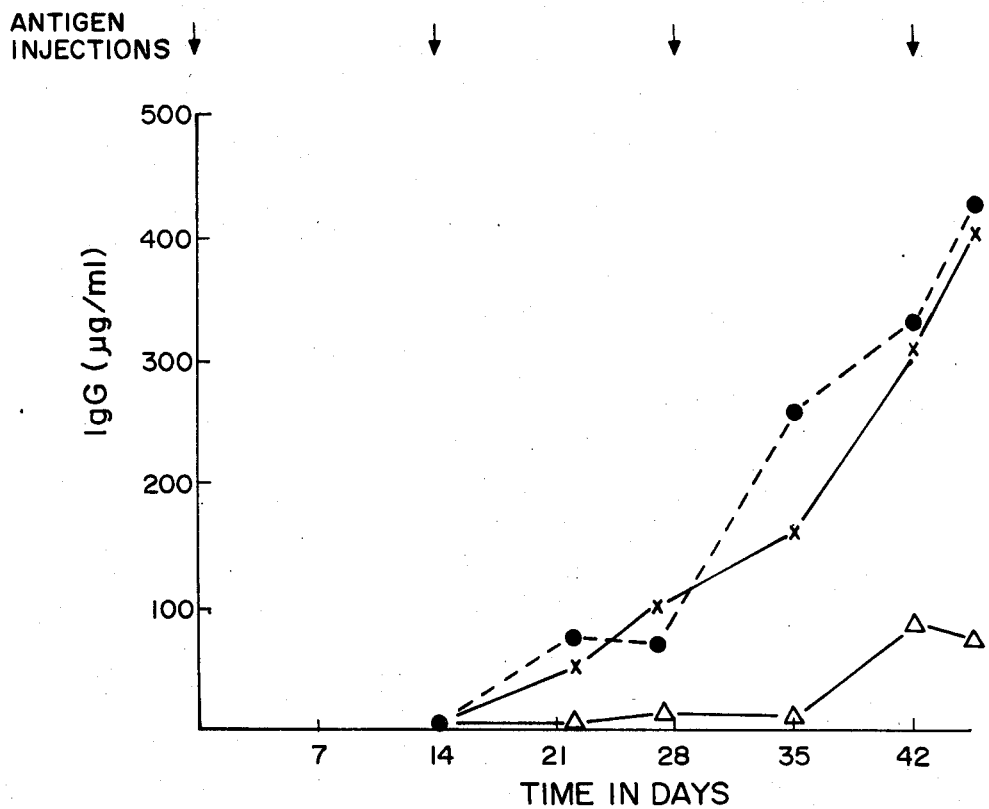
FIG. 2 shows the levels of antimyoglobin IgG in the bloodstream of mice with and without injection of GK1.5 Mab.
Figure 3:
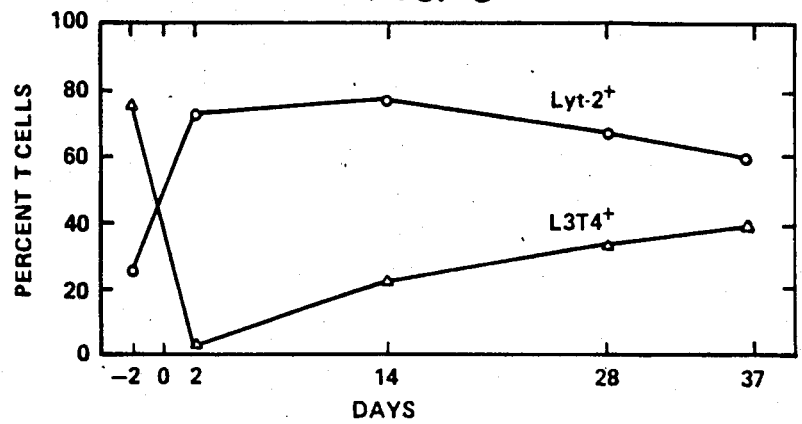
Figure 4B:
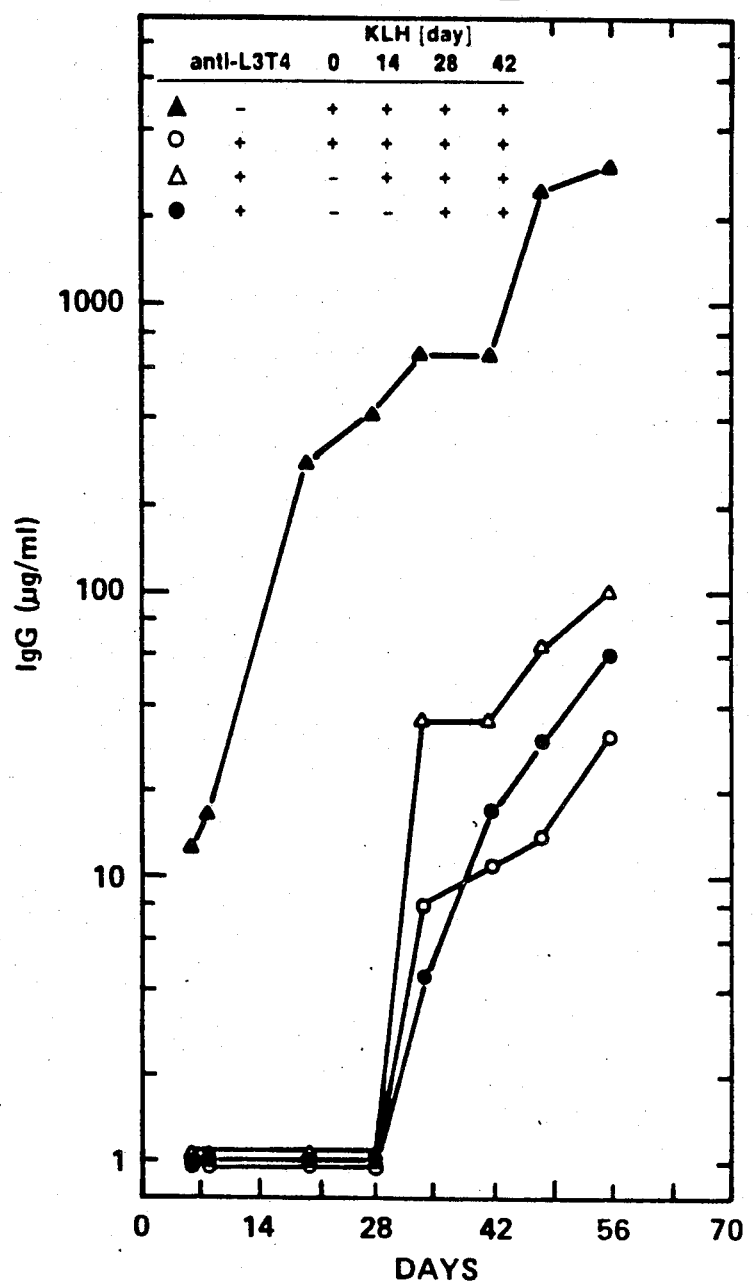

Experimental and control groups of three mice each were similar to those used in Example 1. All groups received 100 μg myoglobin on day 0 and booster injections of 100 μg myoglobin every 14 days thereafter. On day 14, 100 μg of GK1.5-secreted Mab or control injections were administered and sera were withdrawn at various intervals and assayed by ELISA for IgG specific against myoglobin. The results are shown in FIG. 2, where ELISA units are plotted against time.

The open circles joined by dotted and solid lines show the levels of antimyoglobin IgG in the sera of buffer and α-Thy-injected controls respectively. The solid circles show the IgG levels in the sera of mice injected with GK1.5-secreted Mab. The IgG levels of the control mice rise monotonically as the animals are boosted. However, the mice injected at day 14 with GK1.5 fail to show the IgG secondary response to the boosting antigen injections.

EXAMPLE 3

ELISA Assay

For total antimyoglobin Ig: microtiter plates (Dynatech Laboratories, Alexandria, VA) were coated with 100 μg/ml sperm whale myoglobin in PBS for 1 hour at room temperature or overnight at 4° C., and washed with PBS. The remaining nonspecific binding sites were saturated with 3% BSA in PBS, and the plates were washed. Fifty μl of the serum dilutions were added, and the plates incubated for 2 hr at room temperature, and then washed with washing buffer containing Tween 20.

Bound Ig was detected using 100-200 μl diluted peroxidas-coupled goat anti-mouse Ig (GAMIg), incubating at 2 hours at room temperature, and then washing 3 times with washing buffer. The detection solution, OPD/H2O2 was added to each well and incubated for 5 min, and the OD492 of each well was measured by a Dynatech ELISA reader. OD units were correlated with μg protein by standard procedures.

For IgG: the procedure was identical to that above except that labeled goat anti-mouse-IgG was used instead of total goat anti-mouse-Ig.

I claim:

1. A method of conferring immunotolerance to a specific antigen which comprises administering to a subject in need of such tolerance, simultaneous administrations of an effective amount of said antigen and an effective amount of an antibody or derivative thereof which binds to L3T4 or its equivalent, formulated in a pharmaceutically acceptable carrier.

2. The method of claim 1 wherein the subject has previously been exposed to said antigen.

3. The method of claim 1 wherein the antibody or derivative thereof which binds to L3T4 or its equivalent is a monoclonal antibody.

4. The method of claim 1 wherein the antibody or derivative thereof which binds to L3T4 or its equivalent is an immunotoxin.

5. The method of claim 1 wherein the antibody or derivative thereof which binds to L3T4 or its equivalent is specific against Leu3 or T4.

6. A method of ameliorating the symptoms of allergy which comprises simultaneously administering to a susceptible subject an effective amount of antibody or derivative thereof which binds to L3T4 or its equivalent or a pharmaceutical composition thereof, and a normally allergy generating amount of allergen, formulated in a pharmaceutically acceptable carrier.

7. The method of claim 6 wherein the subject has previously been exposed to said antigen.

8. The method of claim 6 wherein the antibody or derivative thereof which binds to L3T4 or its equivalent is a monoclonal antibody.

9. The method of claim 6 wherein the antibody or derivative thereof which binds to L3T4 or its equivalent is an immunotoxin.

10. The method of claim 6 wherein the antibody or derivative thereof which binds to L3T4 or its equivalent is specific against Leu3 or T4.

11. A method of suppressing an immunological response to an immunogenic material which comprises simultaneously administering to a subject an effective amount of antibody or derivative thereof which binds to L3T4 or its equivalent or pharmaceutical composition thereof, and a normally immunogenic amount of said immunogen, formulated in a pharmaceutically acceptable carrier.

12. The method of claim 11 wherein the subject has previously been exposed to said immunogen.

13. The method of claim 11 wherein the antibody or derivative thereof which binds to L3T4 or its equivalent is a monoclonal antibody.

14. The method of claim 11 wherein the antibody or derivative thereof which binds to L3T4 or its equivalent is an immunotoxin.

15. The methods of claim 11 wherein the antibody or derivative thereof which binds to L3T4 or its equivalent is specific against Leu3 or T4.

16. A kit for conferring immunotolerance to an antigen, which kit comprises a container containing a suitable amount of said antigen in a pharmaceutically acceptable excipient and a container containing antibody or derivative thereof which binds to L3T4 or its equivalent in a pharmaceutically acceptable excipient.

17. A pharmaceutical composition for conferring immunotolerance to an antigen which comprises an effective amount of said antigen and an effective amount of antibody or derivative thereof which binds to L3T4 or its equivalent in admixture with one or more pharmaceutically acceptable excipients.

18. The method of claim 1 wherein said subject has been previously exposed to said antigen.

19. The method of claim 6 wherein said subject has been previously exposed to said allergen.

20. The method of claim 11 wherein said subject has been previously exposed to said immunogen.

* * * * *